US010939803B2

(12) United States Patent
Viebach et al.

(10) Patent No.: US 10,939,803 B2
(45) Date of Patent: Mar. 9, 2021

(54) ENDOSCOPE HEAD AND ENDOSCOPE

(71) Applicant: DIGITAL ENDOSCOPY GMBH, Friedberg (DE)

(72) Inventors: Thomas Viebach, Waidhofen (DE); Fritz Pauker, Diedorf (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 697 days.

(21) Appl. No.: 15/101,391

(22) PCT Filed: Nov. 28, 2014

(86) PCT No.: PCT/EP2014/075902
§ 371 (c)(1),
(2) Date: Sep. 2, 2016

(87) PCT Pub. No.: WO2015/082328
PCT Pub. Date: Jun. 11, 2015

(65) Prior Publication Data
US 2017/0127915 A1    May 11, 2017

(30) Foreign Application Priority Data
Dec. 2, 2013   (DE) .................. 10 2013 224 683.8

(51) Int. Cl.
*A61B 1/00*       (2006.01)
*A61B 1/005*      (2006.01)
(Continued)

(52) U.S. Cl.
CPC ........ *A61B 1/00098* (2013.01); *A61B 1/0008* (2013.01); *A61B 1/0011* (2013.01);
(Continued)

(58) Field of Classification Search
CPC ... A61B 1/0051; A61B 1/0055; A61B 1/0057; A61B 1/008; A61B 1/05; A61B 1/051
See application file for complete search history.

(56) References Cited

U.S. PATENT DOCUMENTS 3,549,806 A   12/1970 Wood
3,605,725 A    9/1971 Bentov
(Continued)

FOREIGN PATENT DOCUMENTS

CN    1286664 A    3/2001
CN    2762381 Y    3/2006
(Continued)

OTHER PUBLICATIONS

Machine translation of JP S61-118713.*
(Continued)

*Primary Examiner* — Alexandra L Newton
(74) *Attorney, Agent, or Firm* — Knobbe, Martens, Olson & Bear, LLP

(57) ABSTRACT

The invention relates to an endoscope head on a deflecting end of an endoscope, comprising an MID (molded interconnect device) molded element (1) comprising at least one conducting path (21-28) applied on the same; at least one electronic instrument (3) which is seated in the MID molded element (1) and can be electrically supplied by said at least one conducting path (21-28) thereof; and a sensor (6).

The invention further relates to an endoscope head on a deflecting end of an endoscope, comprising an endoscope head body (1) with at least one conducting path (21-28) applied on the same; at least one electronic instrument (3) which is seated in the endoscope head body (1) and can be electrically supplied by said at least one conducting path (21-28) thereof; and at least one pulling cable (4) whose pulling cable anchoring (41) is seated in the endoscope head body (1); wherein the at least one pulling cable (4) is
(Continued)

electrically connected to the at least one conducting path (21-28) of the endoscope head body (1).

6 Claims, 5 Drawing Sheets

(51) Int. Cl.
| | |
|---|---|
| *A61B 1/015* | (2006.01) |
| *A61B 1/018* | (2006.01) |
| *A61B 1/05* | (2006.01) |
| *A61B 1/06* | (2006.01) |
| *A61B 8/12* | (2006.01) |

(52) U.S. Cl.
CPC ...... *A61B 1/00011* (2013.01); *A61B 1/00027* (2013.01); *A61B 1/0057* (2013.01); *A61B 1/015* (2013.01); *A61B 1/018* (2013.01); *A61B 1/051* (2013.01); *A61B 1/0684* (2013.01); *A61B 8/12* (2013.01)

(56) References Cited

U.S. PATENT DOCUMENTS

| | | | |
|---|---|---|---|
| 4,241,729 | A | 12/1980 | Aoshiro |
| 4,404,963 | A | 9/1983 | Kohri |
| 4,415,767 | A | 11/1983 | Gill et al. |
| 4,670,009 | A | 6/1987 | Bullock |
| 5,245,133 | A | 9/1993 | DeCarlo et al. |
| 5,569,157 | A | 10/1996 | Nakazawa et al. |
| 5,588,950 | A | 12/1996 | Sano |
| 5,630,419 | A | 5/1997 | Ranalletta |
| 6,383,132 | B1 | 5/2002 | Wimmer |
| 6,547,722 | B1 | 4/2003 | Higuma et al. |
| 6,582,361 | B2 | 6/2003 | Hirano |
| 6,716,160 | B2 | 4/2004 | Mitsumori |
| 7,179,223 | B2 | 2/2007 | Motoki et al. |
| 7,198,599 | B2 | 4/2007 | Goto et al. |
| 7,841,880 | B2 | 11/2010 | Ikeda |
| 2001/0025135 | A1 | 9/2001 | Naito et al. |
| 2002/0040180 | A1 | 4/2002 | Hirano |
| 2002/0115907 | A1 | 8/2002 | Mitsumori |
| 2003/0092965 | A1 | 5/2003 | Konomura |
| 2004/0015050 | A1 | 1/2004 | Goto et al. |
| 2004/0147807 | A1* | 7/2004 | Viebach ............... A61B 1/0008 600/129 |
| 2005/0004434 | A1 | 1/2005 | Bob et al. |
| 2006/0074383 | A1* | 4/2006 | Boulais ............... A61B 1/0052 604/95.04 |
| 2006/0116550 | A1 | 6/2006 | Noguchi |
| 2006/0135851 | A1 | 6/2006 | Yamazaki |
| 2006/0199999 | A1 | 9/2006 | Ikeda |
| 2006/0252993 | A1 | 11/2006 | Freed |
| 2007/0156018 | A1 | 7/2007 | Krauter et al. |
| 2007/0221701 | A1 | 9/2007 | Ortiz |
| 2007/0282371 | A1 | 12/2007 | Lee |
| 2009/0209820 | A1 | 8/2009 | Tanaka |
| 2009/0286412 | A1 | 11/2009 | Ikeda |
| 2010/0168560 | A1 | 7/2010 | Hauck et al. |
| 2011/0082494 | A1* | 4/2011 | Kerr ..................... A61B 17/295 606/205 |
| 2011/0288372 | A1* | 11/2011 | Petersen ............. A61B 1/0008 600/109 |
| 2011/0313252 | A1 | 12/2011 | Lin |
| 2012/0170767 | A1 | 7/2012 | Astrom et al. |
| 2012/0209068 | A1 | 8/2012 | Hosaka |
| 2014/0135576 | A1* | 5/2014 | Hebert ................ A61B 1/0057 600/109 |
| 2014/0148646 | A1 | 5/2014 | Inada |
| 2015/0057537 | A1 | 2/2015 | Dillon et al. |
| 2015/0173711 | A1 | 6/2015 | Hiraoka |

FOREIGN PATENT DOCUMENTS

| | | | |
|---|---|---|---|
| CN | 102307510 | A | 1/2012 |
| CN | 102401995 | A | 4/2012 |
| CN | 102697445 | A | 10/2012 |
| CN | 202748535 | U | 2/2013 |
| CN | 103153152 | A | 6/2013 |
| CN | 103211566 | A | 6/2013 |
| DE | 69 05 185 | U | 4/1972 |
| DE | 34 46 698 | A1 | 7/1985 |
| DE | 196 27 016 | C1 | 2/1998 |
| DE | 697 25 670 | T2 | 7/2004 |
| DE | 101 48 099 | B4 | 6/2006 |
| DE | 10 2009 060 500 | | 7/2011 |
| DE | 102010034623 | | 2/2012 |
| DE | 10 2012 00933 | | 11/2013 |
| EP | 0 028 396 | B1 | 4/1981 |
| EP | 0055394 | | 7/1982 |
| EP | 00161834 | A1 | 11/1985 |
| EP | 1475031 | | 11/2004 |
| EP | 1 759 626 | A2 | 3/2007 |
| ES | 2 356 497 | | 4/2011 |
| JP | S 48 27116 | | 8/1973 |
| JP | 60249114 | A | 12/1985 |
| JP | 61-118713 | A | 6/1986 |
| JP | S62-227312 | A | 10/1987 |
| JP | H 06254049 | | 9/1994 |
| JP | 10-225439 | | 8/1998 |
| JP | H11 244225 | | 9/1999 |
| JP | A-2001-061772 | | 3/2001 |
| JP | 2001510696 | | 8/2001 |
| JP | 2002-160691 | | 6/2002 |
| JP | 2002 291699 | | 10/2002 |
| JP | 2003 190085 | A | 7/2003 |
| JP | 2005006769 | A | 1/2005 |
| JP | 2005 304 586 | A | 11/2005 |
| JP | 2007 111541 | A | 5/2007 |
| JP | 2007 252921 | | 10/2007 |
| JP | 2007313047 | | 12/2007 |
| JP | 2009 505688 | A | 2/2009 |
| JP | 2009 101134 | | 5/2009 |
| JP | 2009 530051 | A | 8/2009 |
| JP | 2009-201762 | A | 9/2009 |
| JP | 2012 245058 | A | 12/2012 |
| WO | WO 00/13569 | A1 | 3/2000 |
| WO | WO 00/33727 | | 6/2000 |
| WO | WO 2005/094665 | A2 | 10/2005 |
| WO | 2008/056642 | A1 | 5/2008 |
| WO | WO 2009/008596 | | 1/2009 |
| WO | WO 2001/114772 | A1 | 9/2011 |
| WO | WO 2011/108157 | A1 | 9/2011 |
| WO | WO 2013/129204 | | 9/2013 |

OTHER PUBLICATIONS

Mar. 2, 2015 Int'l Search Report from related PCT App. No. PCT/EP2014/077938 (3 pgs).
Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Anonymous: "Products I BMP-TAPPI ", , Jun. 30, 2013 (Jun. 30, 2013), XP055394249, Gefunden im Internet: URL:https://web. archive.org/web/20130630082009/http:// www.bmp-tappi.com:80/ products [gefunden am Jul. 27, 2017].
Anonymous: "10. Tappo per innesti rapidi femmina", , Jun. 22, 2013 (Jun. 22, 2013), XP055394266, Gefunden im Internet: U RL : https ://web.arch ive.o rglwebl 201 306221 61 7 34lhTtpl www. bmp-tappi. it:80/po rtfol io_item/tappo-per-i n nesti-rapidifemmina [gefunden am Jul. 27, 2017].
Search Report for Application No. 2015800056419 in 2 pages.
Search Report for Application No. 2014800410593 in 2 pages.
Search Report for Application No. 201480076051 in 2 pages.
Office Action dated Sep. 4, 2017 in 7 pages for Chinese Application No. 201580005641.9.
International Search Report dated Oct. 8, 2014 for International Application No. PCT/EP204/065587.

(56) References Cited

OTHER PUBLICATIONS

International Search Report dated Jan. 13, 2015 for International Application No. PCT/EP204/073064.
International Search Report dated Jan. 13, 2015 for International Application No. PCT/EP204/073066.
International Search Report dated Jan. 19, 2015 for International Application No. PCT/EP2014/073065.
International Search Report dated Mar. 24, 2015 for International Application No. PCT/EP2014/075902.
Office Action of corresponding Chinese Patent Application No. 201480074685.2—11 pages (dated Apr. 16, 2019).
Search Report of corresponding Chinese Patent Application No. 201480074685.2—3 pages (dated Apr. 8, 2019).
Office Action for corresponding Japanese Patent Application No. 2016-536635—4 pages (dated Sep. 17, 2017).
Office Action for corresponding Japanese Patent Application No. 2016-536635—5 pages (dated Aug. 20, 2018).
Decision of Grant for corresponding Japanese Patent Application No. 2016-536635—4 pages (dated Apr. 23, 2019).
First Office Action of corresponding Chinese Patent Application No. 201480074685.2—13 pages (dated Jun. 7, 2017).
Office Action of corresponding Japanese Patent Application No. 2016-536635—3 pages (dated Sep. 19, 2019).
Search Report of corresponding Chinese Patent Application No. 201480074685.2—4 pages (dated May 27, 2017).

\* cited by examiner

ENDOSCOPE HEAD AND ENDOSCOPE

The present invention relates to an endoscope head and to an endoscope provided with the same. More precisely, the present invention relates to an improved endoscope head that can be used at the distal end of a deflecting portion of an endoscope.

BACKGROUND OF THE INVENTION

For some time there has been a trend in endoscopy towards increasingly smaller endoscopes. In this connection, also an endoscope head arranged at the distal end of a deflecting portion of an endoscope is designed smaller and smaller. In doing so, it becomes more and more difficult to integrate the devices used in endoscopy, such as for example LED, camera and/or working channel, etc. into the endoscope head.

The present invention shall demonstrate a new way of making it possible to further minimize endoscopes and endoscope heads through an innovative design of an endoscope head.

OBJECT OF THE INVENTION

It is thus an object of the present invention to create an improved endoscope head. Furthermore, an improved endoscope shall be created.

Solution

With regard to the endoscope head, the object is achieved by an endoscope head according to claim 1. An alternative endoscope head is shown in claim 7. With regard to the endoscope, the object is achieved by an endoscope according to claim 11. Advantageous further developments are described in the dependent claims.

Hence, the invention relates to an endoscope head on a deflecting end of an endoscope, comprising an MID molded element having conducting paths applied thereon; at least one electronic instrument which is seated in the MID molded element and can be electrically supplied by the conducting paths thereof; and a sensor. Such an endoscope head can be cost-effectively produced and created as a particularly small body which is basically constructed as a three-dimensional circuit board. Thus, the electronic instrument can be conveniently linked to the conducting paths of this three-dimensional circuit board. The functions of the endoscope head can be guaranteed in the smallest space.

The MID molded element can comprise a working channel opening and/or at least one flushing channel opening in the endoscope head. Already during production, the MID molded element can be designed in such a manner, for example by means of injection molding, that a working channel opening and/or at least one flushing channel opening is/are formed. Subsequent drilling or other production processes for forming the working channel opening and/or the flushing channel opening need not be provided.

In the endoscope head, the sensor can be an optical sensor or an acoustic sensor. A variety of sensors can be used. The optical sensor can be a camera. The acoustic sensor can be an ultrasonic sensor.

The endoscope head can have at least one pulling cable whose pulling cable anchoring is seated in the MID molded element. Thus, the MID molded element can be deflected by actuating the pulling cable and can be bent in different directions.

In the endoscope head, on the distal end of the MID molded element, there can be a cavity, in which the at least one electronic instrument is seated on a conducting path of the MID molded element, wherein the cavity is filled with a transparent and hardened casting compound. The bottom of the cavity can have a three-dimensional shape with elevations and depressions and basically forms a surface of the three-dimensional circuit board. The casting compound protects the conducting paths and the electronic components and electronic instruments arranged thereon and, thus, the surface of the three-dimensional circuit board. The casting compound is translucent. Preferably, the casting compound can be designed so as to not affect the signal transmission from and to the electronic instrument.

The at least one electronic instrument can be one, preferably two LED(s). On the distal end of the MID molded element, a camera module can be arranged as an optical sensor adjacent to the cavity, wherein the camera module is shielded towards the cavity.

Alternatively, the at least one electronic instrument can be an ultrasonic emitting means. On the distal end of the MID molded element, an acoustic sensor can be arranged adjacent to the cavity, wherein the acoustic sensor is shielded towards the cavity.

The shielding prevents that the sensor directly receives signals output from the LED/ultrasonic emitting means and is influenced by these direct signals.

It is also possible to use more than two electronic instruments.

The covering surface of the transparent and hardened casting compound can extend in a planar manner or can be curved inwards on the distal side of the MID molded element. A planar covering surface is easy to clean. A covering surface curved inwards supports the shielding against direct signals.

Alternatively, the invention relates to an endoscope head on a deflecting end of an endoscope, comprising an endoscope head body having at least one conducting path applied thereon; at least one electronic instrument which is seated in the endoscope head body and can be electrically supplied by the at least one conducting path thereof; and at least one pulling cable whose pulling cable anchoring is seated in the endoscope head body; wherein the at least one pulling cable is electrically connected to the at least one conducting path of the endoscope head body.

This leads to a cost-effectively designed electric supply of the endoscope head combined with a space-saving design. A space-consuming electric supply cable for the electronic instrument need not be provided.

In the endoscope head, the at least one pulling cable can be electrically connected to the at least one conducting path of the endoscope head body via its pulling cable anchoring. The pulling cable anchoring can be an electrically conductive body electrically connecting the conducting path and the pulling cable.

In the endoscope head, four pulling cables can be anchored to the endoscope head body, two pulling cables of which are electrically connected to the at least one conducting path of the endoscope head body. Two of the four pulling cables can be electrically conductive. The mode of operation is the same as in the case of a conventional endoscope head where the deflection movement is controlled by means of four pulling cables. It is also possible that all four pulling cables are electrically conductive.

The number of pulling cables is not restricted.

The endoscope head body can be an MID molded element.

Thus, the endoscope head body can be produced in a cost-effective and environmentally friendly manner and can be formed in a versatile manner and with a great freedom of design. Therefore, any endoscope head body shapes are possible. A further miniaturization of the endoscope heads is realized. The amount of materials used for producing the endoscope head body is restricted to a minimum, which leads to savings in material and the number of components. The number of assembly steps is reduced. The accuracy of molding and, thus, also the reliability of the endoscope head are drastically increased. For the endoscope head body, materials which can be unproblematically disposed of can be used, in contrast to conventional circuit boards. The axial length of the endoscope head body can be shortened.

The features of the invention can be combined in a suitable manner. Hereinafter, the invention will be explained in detail by means of examples.

BRIEF DESCRIPTION OF THE DRAWINGS

FIG. 1 shows an endoscope head with pulling cables according to an embodiment of the invention, wherein

FIG. 2 shows the endoscope head with pulling cables according to the embodiment of FIG. 1, wherein

FIG. 4 shows an endoscope head body of FIG. 3, into which pulling cables are hung in.

Below, the present invention will be described in detail by means of the drawings.

Figure 1C:
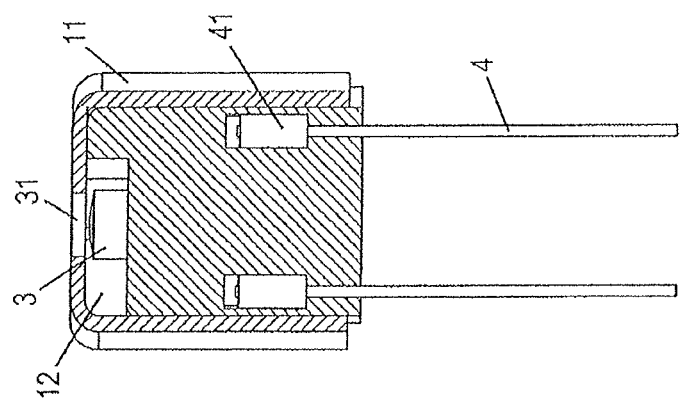
FIG. 1(B) shows a side view and FIG. 1(C) shows a sectional view along a line A-A in FIG. 1(B).
Figure 1B:
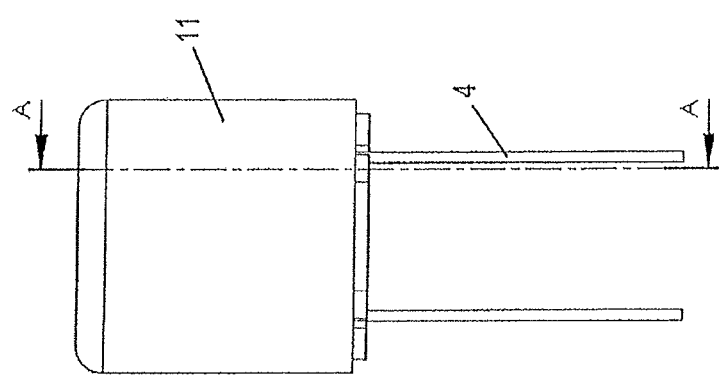
Figure 1A:
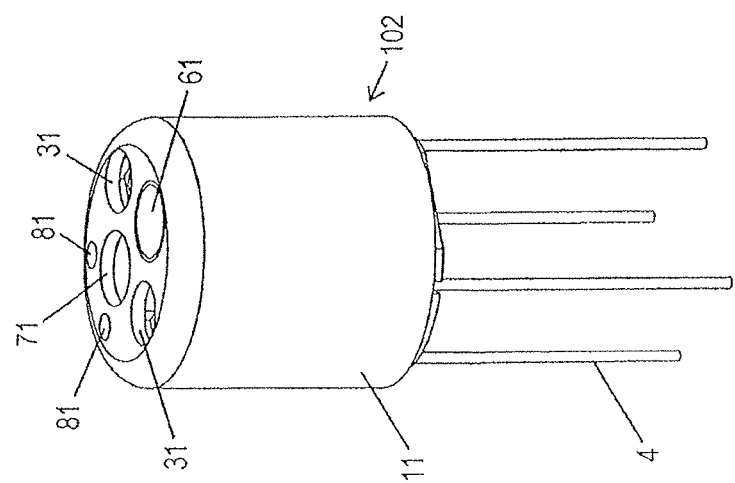
FIG. 1(A) shows a schematically perspective view.
Figure 2B:
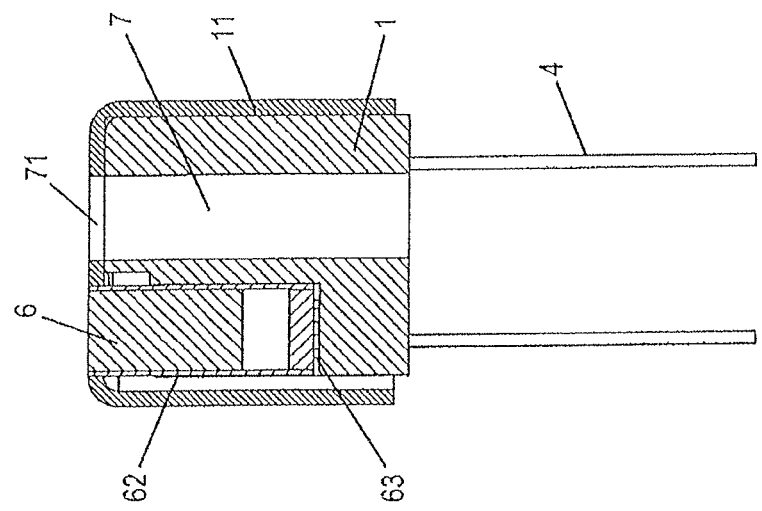
FIG. 2(A) shows a side view and FIG. 2(B) shows a sectional view along a line D-D in FIG. 2(A).
Figure 2A:
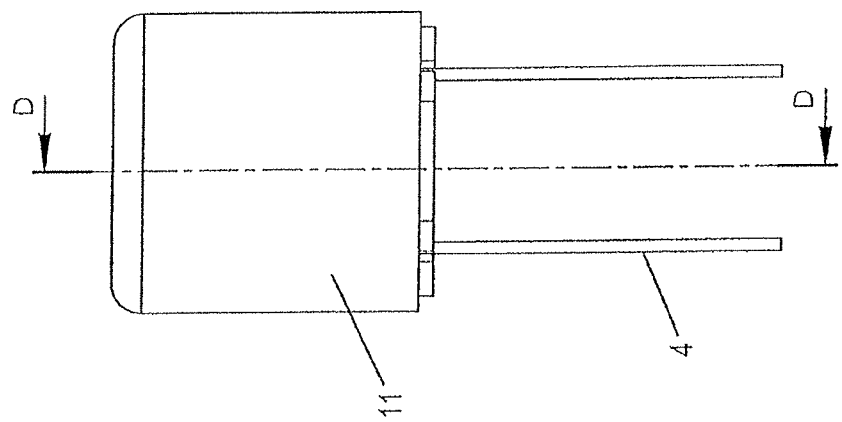

FIG. 1 shows an endoscope head with pulling cables according to an embodiment of the invention, wherein FIG. 1(A) shows a schematic perspective view, FIG. 1(B) shows a side view and FIG. 1(C) shows a sectional view along a line A-A in FIG. 1(B). FIG. 2 shows the endoscope head with pulling cables according to the embodiment of FIG. 1, wherein FIG. 2(A) shows a side view and FIG. 2(B) shows a sectional view along a line D-D in FIG. 2(A).

On a (non-depicted) catheter portion the endoscope according to the invention comprises a deflecting portion (not depicted either). The deflecting portion extends from a (non-depicted) ring element on the proximal side of the deflecting portion to an endoscope head 102 on the distal side of the deflecting portion. Hence, the endoscope head 102 is arranged at a deflecting end of the endoscope.

The endoscope head 102 according to the invention comprises an MID molded element (molded interconnected device) 1 as endoscope head body. The MID molded element 1 is a plastic carrier made of an organic polymeric material, which can be produced, for example, by injection molding. The MID molded element 1 consists, for example, of a thermoplastic or a duroplastic. In particular, the MID molded element 1 can be produced from polypropylene (PP), acrylonitrile butadiene styrene (ABS), polycarbonate (PC), polyethylene terephthalate (PET), polybutylene terephthalate (PBT), polyamide (PA), polyphenylene sulfide (PPS), polysulfone (PSU), polyethersulfone (PES), polyetherimide (PEI), etc. These specifications are merely examples and other materials can be used for the MID molded element 1.

The MID molded element 1 is a cylinder-like element whose central axis extends from a proximal side to a distal side. On the proximal side, the MID molded element 1 can be connected to the deflecting portion. The distal side of the MID molded element 1 constitutes the distal side of the endoscope head 102.

On its distal side and on its side surfaces, the MID molded element 1 is surrounded by a cap 11. The cap 11 is a hollow cylinder provided with a bottom, wherein the bottom of the cap, when mounted to the MID molded element 1, constitutes the distal side of the endoscope head 102. The inner diameter of the cap 11 is such that the cap is smoothly seated on the outer diameter of the MID molded element 1. Alternatively, a press fit can be provided. In a further alternative, the cap 11 can comprise an inner thread on the inner circumferential surface and can be screwed onto an outer thread on the MID molded element 1. Other form-fitting connections between the cap 11 and the MID molded element 1 are possible.

On the distal front face, the cap 11 has distal openings 31 for a signal output of a subsequently described LED chip 3, a distal opening for a camera window 61 for a signal input for a subsequently described camera 6, a distal working channel opening 71 and distal flushing channel openings 81.

When the cap 11 is mounted to the MID molded element 1, the MID molded element 1 projects beyond the cap 11 on the proximal side. A distal end portion of a non-depicted tube element of the deflecting portion is placed on the outer circumference of the MID molded element 1 proximally projecting from the cap 11. The distal front face of the tube element abuts in a sealed manner on the proximal end surface of the cap 11. The distal front face of the tube element can be bonded with the proximal end surface of the cap 11.

Figure 3:
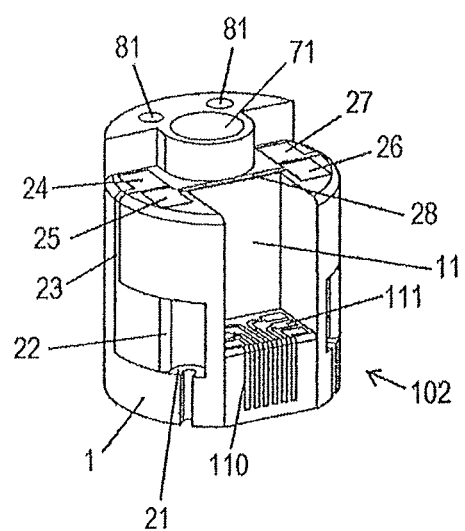
FIG. 3 shows an endoscope head body for the endoscope head according to the embodiment of FIG. 1.

FIG. 3 shows the MID molded element 1 as the endoscope head body for the endoscope head according to the embodiment of FIG. 1.

The MID molded element 1 is provided with one or plural metallic conducting paths 21-28, 110, 111. The conducting paths 21-28, 110, 111 can be applied on the MID molded element 1 by means of two-component injection molding, hot stamping, a mask irradiation method, laser structuring methods, film rear-injection or another suitable method. Basically, the MID molded element 1 provided with the conducting paths 21-28, 110, 111 constitutes a three-dimensional circuit board.

More precisely, on the MID molded element 1, conducting paths 21-28 are integrally formed for subsequently described LED chips 3, and conducting paths 110, 111 are integrally formed for a camera module 6.

Hereinafter, the conducting paths will be described in greater detail.

In consideration of FIG. 3, the MID molded element 1 formed as three-dimensional circuit board has several planes, which may be designated as first plane for a pulling cable anchoring body connection, second plane for a camera connection, third plane for an LED connection, and fourth plane as distal end surface. The first plane and the second plane can be displaced with respect to each other, or can be on the same level.

At a distance to its proximal end surface, the MID molded element 1 has, on its outer circumferential surface, respective cavities for the pulling cable anchoring bodies 41 described below. Each of said cavities is dimensioned such that there is enough space for a pulling cable anchoring body 41 and has, on its proximal side, a supporting surface area on which the pulling cable anchoring body 41 can be supported in the proximal direction. Thus, the supporting surface area extends horizontally, i.e. in parallel to the proximal end surface of the MID molded element 1, and is located at the above-described first plane. The cavities are adapted to the shape of the pulling cable anchoring body 41 and, in the present example, are designed in the form of a cylinder. Thus, in the present example, the MID molded element 1 has four such supporting surface areas. Each supporting surface area is centrically provided with a channel-type groove extending toward the proximal end surface of the MID molded element 1, said groove receiving the pulling cable 4 connected to the pulling cable anchoring body 41 when the pulling cable anchoring body 41 is inserted at the supporting surface area. The diameter of the supporting surface is, in any case, larger than the diameter of the pulling cable 4. Should e.g. a quadrangular pulling cable anchoring body be used, so that the cavity has a quadrangular shape, a square supporting surface area is obtained.

The supporting surface area is formed with a first conducting path 21 at least for two pulling cable anchoring bodies (in FIG. 3, on the two cavities facing the observer). A second conducting path 22, which at first extends vertically upwards, is connected to the conducting path 21, respectively; said second conducting path 22 is integrally formed on the edge of the cavity, extends horizontally away from the cavity when reaching the upper edge of the cavity and, finally, as is shown in FIG. 3, passes into a third conducting path 23 extending vertically upwards. The third conducting path 23 is connected to a planar conducting path section 24, which is integrally formed on the third plane of the MID molded element 1. The planar conducting path section 24 forms an anode for a first LED chip 3. Adjacent thereto, and without contact to the planar conducting path section 24, a planar conducting path section 25 is integrally formed on the third plane of the MID molded element 1. The planar conducting path section 25 forms a cathode for the first LED chip 3. In consideration of FIG. 3, the conducting path sections 21-25 are located on the left side of a camera accommodation space provided for a camera connection above the second plane. On the—in view of FIG. 3—right side of the camera accommodation space, a conducting path structure similar to that of the left side is formed. In FIG. 3, a cavity for a pulling cable anchoring body is shown, on the right side next to the second plane for a camera connection, said cavity also being formed with a conducting path like the first conducting path 21. Said conducting path is connected to a planar conducting path section 26 on the third plane. The planar conducting path section 26 forms a cathode for a second LED chip 3. Adjacent to and without contact to the planar conducting path section 26, a planar conducting path section 27 is integrally formed on the third plane of the MID molded element 1. The planar conducting path section 27 forms an anode for the second LED chip 3. The planar conducting path section 25 is connected to the planar conducting path section 26 by a web 28, as is shown in FIG. 3. The planar conducting path section 27 is connected to the planar conducting path section 24, which is not shown in the representation of FIG. 3.

Conducting path sections 110 are molded on the proximal side of the camera accommodation space, i.e. on the second plane of the MID molded element 1, and end in planar conducting path sections 111 for a connection with a camera module 6. The planar conducting path sections 111 are also formed on the second plane of the MID molded element 1. The conducting path sections 110 are electrically connected to a (non-depicted) camera cable terminal provided on the proximal surface of the MID molded element 1. A supply cable which is guided in the deflecting portion is inserted into said camera cable terminal.

In addition, on the fourth plane, the MID molded element 1 comprises a distal working channel opening 71 as extension of a non-depicted working channel element for e.g. micro tools and at least one distal flushing channel opening 81 of at least one flushing channel. In the present example, the MID molded element 1 comprises two distal flushing channel openings 81 for two flushing channels. To be more exact, a working channel end section and two flushing channel end sections are provided as through holes in the MID molded element 1 in the axial direction in parallel to the central axis of the MID molded element 1 in the area which is not taken up by the camera accommodation space and the area of the conducting paths. As is shown in FIG. 1, the working channel end section is arranged adjacent between the two flushing channel end sections. In the distal front face of the MID molded element 1, the working channel end section has the distal working channel opening 71 and the two flushing channel end sections each have a distal flushing channel opening 81. The working channel end section is arranged in parallel and adjacent to the camera accommodation space. The flushing channel end sections are arranged radially outside the working channel end section, but the invention is not restricted thereto.

Figure 4:
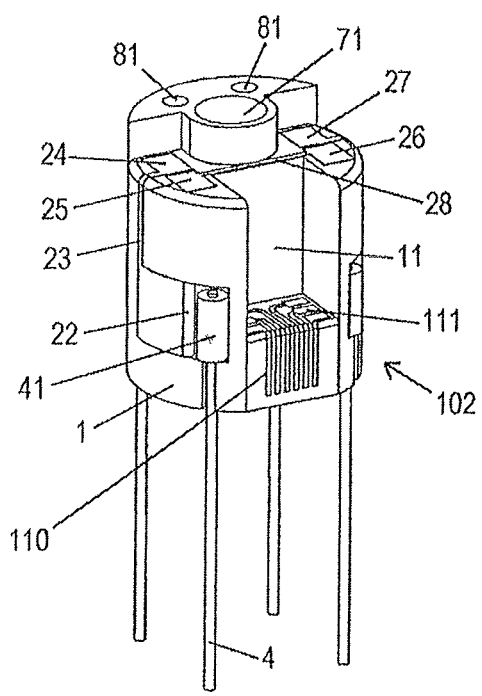

In the following, the further construction of the endoscope head 102 will be described in detail. FIG. 4 shows an endoscope head body of FIG. 3, into which pulling cables are fitted.

A pulling cable anchoring body 41 is inserted into each lateral cavity on the MID molded element 1 such that its proximal side abuts on the supporting surface area, so that a pulling force acting in the proximal direction is transferred from the pulling cable anchoring body 41 to the supporting surface area and, thus, to the MID molded element 1. Every pulling cable anchoring body 41 is firmly arranged on the distal end of a pulling cable 4 in the known manner.

In the present example, two lateral cavities on the MID molded element 1 are provided with conducting paths, as has been described above. An electrically conductive pulling cable anchoring body 41 with pulling cable 4 is arranged in each of said cavities. In the present example, two of the four supporting surface areas are lined with a conducting path section, respectively.

The two pulling cable anchoring bodies 41, the front ones in FIG. 4, which are seated on a conducting path section 2, respectively, and the pulling cables 4 connected to the same are electrically conductive. Each conducting path section 2 on which an electrically conductive pulling cable anchoring body 41 is seated forms an electrical connection for an electronic instrument. Thus, the conducting path sections 21-28 can be supplied with electric current via the electrically conductive pulling cables 4. A direct current supply or an alternating current supply of the electronic instrument(s) is possible thereby. In the present example of FIG. 1, four pulling cables 4 are anchored on the MID molded element, two pulling cables 4 of which are electrically connected to the at least one conducting path 2 of the MID molded element 1.

Such a pulling cable anchoring body 41 can have different shapes, i.e. it may be a barrel nipple, a pear nipple, a ball nipple, etc.

In the present example, the MID molded element 1 has four supporting surface areas for four pulling cable anchoring bodies 41. The invention is not restricted thereto. The endoscope head 102 may comprise three, five or more pulling cable anchoring bodies 41 and the corresponding number of supporting surface areas on the MID molded element 1.

By a non-depicted control member, the endoscope head 102 can be pivoted in any direction in the known manner by means of a pulling movement on the pulling cables 4.

Figure 5:
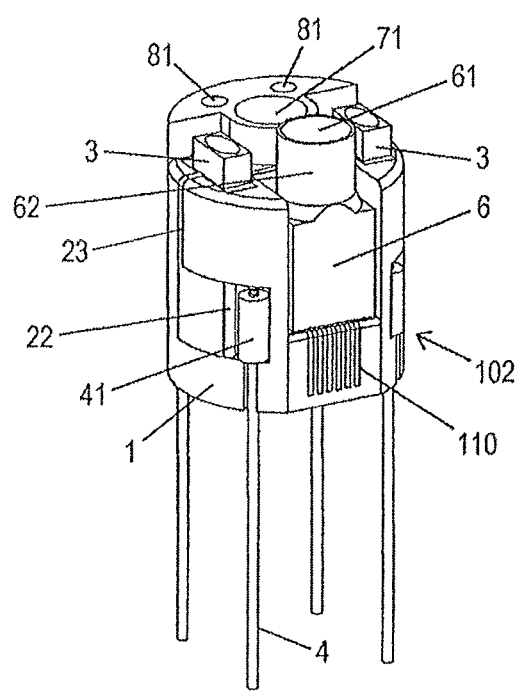
FIG. 5 shows an endoscope head body of FIG. 4 into which a camera module and LED chips are inserted.

FIG. 5 shows an endoscope head body of FIG. 4, into which a camera module and LED chips are inserted.

A first LED chip 3 is arranged on the planar conducting path section 24 (anode) and the planar conducting path section 25 (cathode). A second LED chip 3 is arranged on the planar conducting path section 26 (cathode) and the planar conducting path section 27 (anode). In particular, the LED chips 3 are arranged such that, on the proximal side, their ports face the planar conducting path sections 24-27. The output surface of the LED chips 3 is on their distal side. The output surface of the LED chips 3 is on a plane which is parallel to and spaced apart from the distal end surface (fourth plane) of the MID molded element 1. In other words, the distal end surface (fourth plane) of the MID molded element 1 projects in the distal direction beyond the output surface of the LED chips 3.

The camera module 6 is arranged in the camera accommodation space such that the connecting contacts 63 of the camera module 6 are in contact with the planar conducting path sections 111, see also FIG. 2(B). In particular, the camera module 6 is arranged such that its connecting contacts on the proximal side face the planar conducting path sections 111. A camera window 61 via which image information can be taken is arranged on the distal side. The distal end section of the body of the camera module 6 extends up to the camera window 61 and is surrounded by a cylindrical shield 62.

The shield 62 extends in the distal direction beyond the distal end surface of the MID molded element 1, i.e. it slightly projects from the fourth plane of the MID molded element 1. Thus, the shield 62 extends in the distal direction beyond the horizontal plane of the output surface of the LED chips 3. In this way, the shield 62 provides a shielding of the camera module 6 against the light radiation of the LED chips 3.

The wall thickness of the distal end surface of the cap 11 is selected so as to correspond to the difference in height between the fourth plane of the MID molded element 1 and the distal end side of the shield 62 projecting from the fourth plane of the MID molded element 1. Thus, in the case of the cap 11 being placed on the MID molded element 1, the proximal inner surface of the distal end surface of the cap 11 abuts on the fourth plane of the MID molded element 1, and the distal end side of the shield 62 is approximately in alignment with the distal outer surface of the distal end surface of the cap 11.

Therefore, a hollow space 12 is formed between the proximal inner surface of the distal end surface of the cap 11 and the third plane of the MID molded element 1, i.e. the plane for the LED connection. Said hollow space 12 is limited by the cap 11 at its upper side and (with the cap 11 being put on) is only open at the openings 31 on the distal side, see FIG. 1(C). The openings 31 are arranged exactly above the LED chips 3, respectively.

The hollow space 12 may (but need not) be filled with a casting compound which covers the conducting path sections and the LED chips 3. The casting compound is transparent and curable and has sufficient adhesiveness for adhering to the bottom and to the walls of the hollow space 12.

Method of Manufacturing the Mid Molded Element

The MID molded element 1 including the conducting path(s) as three-dimensional circuit board can be manufactured in different ways.

For example, a two-step molding method can be used.

At first, a plastic carrier is injection-molded as basic body of the MID molded element 1. Subsequently, the conducting path(s) is (are) applied onto the basic body, e.g. by two-component injection molding, hot stamping, mask irradiation or laser structuring, etc.

When doing so, shaping is more or less freely selectable. As endoscope head body, the MID molded element 1 is designed in the form of a cylinder having a small outer diameter such that there remains sufficient space for the working channel and the flushing channel(s).

Further Alternatives

In the present example of FIGS. 1-5, four pulling cables 4 are anchored on the MID molded element 1, two pulling cables 4 of which are electrically connected to the at least one conducting path 2 of the MID molded element 1. The invention can, however, also be applied to an MID molded element 1 where no pulling cable 4 is electrically conductive. The electrical supply of the conducting path 2 is then effected by means of cables running in the deflecting portion 100.

In the present example, the cap 11 is placed onto the MID molded element 1. The cap 11 can also be omitted. In this case, the outer surface and the distal front face of the MID molded element 1 are shaped so as to not show any undercuts, which makes cleaning easier.

In the present example of FIGS. 1-5, the outer surface of the camera module 6 abuts on the inner surface of the cap 11. The MID molded element 1 can also be shaped such that, in the MID molded element 1, a specific camera depression having a distal opening is provided, into which the camera module 6 is inserted from the distal side. The side surfaces of the camera module 6 are then surrounded by the MID molded element 1 except on the distal side. The specific camera depression can be dimensioned to exactly fit the camera module 6. The camera shield 62 projecting from the distal side of the MID molded element 1 is adapted to be lockable on the proximal side in the MID molded element 1 for providing safe support to the camera module 6 in the MID molded element 1 while being easily detachable. Alternatively, the camera module 6 is firmly molded to the MID molded element 1 by a casting compound.

When the cap 11 is omitted, the MID molded element 1 can be formed so as to have a circumferential wall up to the height of the fourth plane. Then, on the distal side, the casting compound forms an end surface constituting the distal end surface of the endoscope head. The distal end surface of the casting compound is formed so as to be curved inwards, but may also be flat, i.e. plane, in a further example. Thus, the covering surface of the transparent and hardened casting compound on the distal side of the MID molded element is curved inwards or extends in a planar manner. An outwardly directed curvature of the distal end surface of the casting compound is also possible. Thus, on the distal end of the MID molded element 1, there is also a space such as the cavity 12, in which at least one electronic instrument 3 is seated on a conducting path 2 of the MID molded element 1, said space being filled with the transparent and hardened casting compound. In this case, too, the shield extends in the distal direction beyond the distal end surface of the MID molded element 1 and slightly projects from the fourth plane of the MID molded element 1 of the distal end surface of the casting compound.

In the MID molded element 1, a working channel section and two flushing channel sections extend in parallel and spaced apart from the central axis of the MID molded element 1. The working channel section can also be arranged on the central axis of the MID molded element 1. Three or more flushing channels can be provided. However, due to the construction being small, a design with one or two flushing channels is preferable. As a further alternative, the working channel section and/or the flushing channels can run obliquely in the MID molded element 1.

In the present example, a camera module 6 is arranged as optical sensor on the MID molded element 1, and LED chips 3 are provided as optical signal transmitters as an example of an electronic instrument. Alternatively, an ultrasonic emitting device can be provided as electronic instrument instead of the LED chips 3, and an acoustic sensor can be arranged instead of the camera module 6, the acoustic sensor being shielded towards the cavity.

When the sensor area is used for another type of sensor, such as an acoustic sensor, the shielding wall portions projecting from the distal end surface of the casting compound may be omitted.

LIST OF REFERENCE SIGNS

1 MID (=molded interconnect device) molded element
11 cap
12 cavity
21-28,
110, 111 conducting path
3 LED chip
31 opening
4 pulling cable
41 pulling cable anchoring body
6 camera module
61 camera window
62 camera shield
63 camera connecting contacts
7 working channel element
71 distal working channel opening
8 flushing channel
81 distal flushing channel opening
102 endoscope head
110 conducting path sections
111 conducting path sections for connecting the camera module

The invention claimed is:

1. An endoscope head for a deflecting end of an endoscope, comprising
an endoscope head body having at least one conducting path applied thereon;
at least one electronic instrument which is seated in the endoscope head body and configured to be electrically supplied by said at least one conducting path; and
at least one pulling cable having an anchor which is seated in the endoscope head body;
wherein the at least one pulling cable is electrically connected to the at least one conducting path of the endoscope head body,
wherein the endoscope head body is a molded interconnect element having the at least one conducting path integrally formed for the at least one electronic instrument, said molded interconnect element having a cavity to arrange the anchor of the at least one pulling cable,
wherein the cavity has a supporting surface on which the anchor of the at least one pulling cable is supported, said supporting surface being formed with the at least one conducting path so that the anchor is in electrical contact to the at least one conducting path.

2. The endoscope head according to claim 1, wherein the at least one pulling cable is electrically connected by its anchor to the at least one conducting path of the endoscope head body.

3. The endoscope head according to claim 1, wherein four pulling cables are anchored to the endoscope head body, two pulling cables of which are electrically connected to the at least one conducting path of the endoscope head body.

4. An endoscope having an endoscope head according to claim 1.

5. The endoscope head according to claim 1, the molded interconnect element comprises at least one of a working channel opening and a flushing channel opening.

6. The endoscope head according to claim 1, wherein the at least one electronic instrument is seated on the at least one conducting path in the cavity.

* * * * *